United States Patent
Clark

(10) Patent No.: US 9,861,383 B2
(45) Date of Patent: Jan. 9, 2018

(54) NEEDLE ASSEMBLY

(75) Inventor: Geoff Clark, Lempster, NH (US)

(73) Assignee: SMITHS MEDICAL ASD, INC., Plymouth, MN (US)

( * ) Notice: Subject to any disclaimer, the term of this patent is extended or adjusted under 35 U.S.C. 154(b) by 1204 days.

(21) Appl. No.: 13/567,122

(22) Filed: Aug. 6, 2012

(65) Prior Publication Data

US 2013/0053791 A1 Feb. 28, 2013

Related U.S. Application Data

(60) Provisional application No. 61/573,093, filed on Aug. 31, 2011.

(51) Int. Cl.
*A61M 5/32* (2006.01)
*A61B 17/34* (2006.01)

(52) U.S. Cl.
CPC ....... *A61B 17/3401* (2013.01); *A61M 5/3293* (2013.01); *A61M 2205/586* (2013.01); *A61M 2205/6045* (2013.01)

(58) Field of Classification Search
CPC ..... A61B 17/3401; A61B 2017/00455; A61M 25/0606; A61M 2205/586; A61M 2205/6045; A61M 2005/1587; A61M 19/00
USPC .................. 604/164.07, 165.01, 165.02, 512
See application file for complete search history.

(56) References Cited

U.S. PATENT DOCUMENTS

| 3,506,007 | A | 4/1970 | Henkin |
| D269,549 | S | 6/1983 | Gross |
| D282,008 | S | 12/1985 | McFarlane |
| D302,589 | S | 8/1989 | McMenamy et al. |
| 5,211,644 | A | 5/1993 | VanBeek et al. |
| 5,215,528 | A | 6/1993 | Purdy |
| 5,545,152 | A | 8/1996 | Funderbuck et al. |
| 5,571,091 | A * | 11/1996 | Davis et al. ............. 604/164.11 |

(Continued)

FOREIGN PATENT DOCUMENTS

| EP | 0583144 | 2/1994 |
| EP | 0792659 | 9/1997 |

(Continued)

OTHER PUBLICATIONS

PCT International Search Report and Written Opinion re PCT/US2012/051652, dated Jan. 21, 2013 by ISA/KR.

(Continued)

*Primary Examiner* — Emily Schmidt

(74) *Attorney, Agent, or Firm* — Louis Woo

(57) ABSTRACT

A needle assembly has a needle hub that has a body to which are formed two plates at opposite sides thereof in a parallel relationship. The plates have respective upper edges and lower edges that lie substantially along respective planes, so that the needle hub may be stably placed onto a surface by means of the respective edges. The plates also prevent the rolling of the needle between the fingers of the clinician when the clinician holds the needle assembly by means of the plates. A partition is formed orthogonally proximate to the front ends of the parallel plates. The connector at the proximal portion of the needle hub is configured to have a non-conventional configuration that allows it to mate only with a counterpart connector that has a complementary non-conventional configuration.

14 Claims, 6 Drawing Sheets

(56) References Cited

U.S. PATENT DOCUMENTS

| | | |
|---|---|---|
| D378,130 S | 2/1997 | Schmidt |
| D378,405 S | 3/1997 | Musgrave et al. |
| 5,651,776 A | 7/1997 | Appling et al. |
| D397,434 S | 8/1998 | Pike |
| 5,853,391 A | 12/1998 | Bell |
| 5,855,230 A | 1/1999 | Guala et al. |
| D417,733 S | 12/1999 | Howell et al. |
| D421,119 S | 2/2000 | Musgrave et al. |
| 6,027,480 A | 2/2000 | Davis et al. |
| 6,197,007 B1 | 3/2001 | Thorne et al. |
| D452,003 S | 12/2001 | Niermann |
| D452,314 S | 12/2001 | Niermann |
| 6,475,190 B2 | 11/2002 | Young |
| 6,506,181 B2 | 1/2003 | Meng et al. |
| D469,870 S | 2/2003 | Niermann et al. |
| D471,980 S | 3/2003 | Caizza |
| 6,558,353 B2 | 5/2003 | Zohmann |
| 6,656,161 B2 | 12/2003 | Young et al. |
| 6,887,417 B1 | 5/2005 | Gawreluk et al. |
| 6,953,448 B2 | 10/2005 | Moulton et al. |
| D523,956 S | 6/2006 | Guala |
| D607,100 S | 12/2009 | Uchida et al. |
| 7,658,725 B2 | 2/2010 | Bialecki et al. |
| D640,785 S | 6/2011 | Lee |
| 7,955,315 B2 | 6/2011 | Feinberg et al. |
| D655,406 S | 3/2012 | Ma et al. |
| D669,577 S | 10/2012 | Holsinger |
| D679,803 S | 4/2013 | Carter |
| 2003/0050611 A1 | 3/2003 | Cindrich |
| 2003/0069542 A1 | 4/2003 | Meng et al. |
| 2004/0167474 A1 | 8/2004 | Meng et al. |
| 2005/0090801 A1 | 4/2005 | Racz et al. |
| 2007/0270758 A1 | 11/2007 | Hanner et al. |
| 2012/0004625 A1* | 1/2012 | Velez-Rivera ............... 604/272 |

FOREIGN PATENT DOCUMENTS

| | | | |
|---|---|---|---|
| EP | 1010439 | 6/2000 | |
| WO | WO 02/45781 A2 | 6/2002 | |
| WO | 2005/044335 | 10/2004 | |
| WO | WO 2008/149205 A1 | 12/2008 | |
| WO | WO 2008157376 A1 * | 12/2008 | ............. A61B 17/34 |

OTHER PUBLICATIONS

Supplementary European Search Report and Search Opinion, dated Jan. 21, 2015, EP Application No. 12827631.8.

* cited by examiner

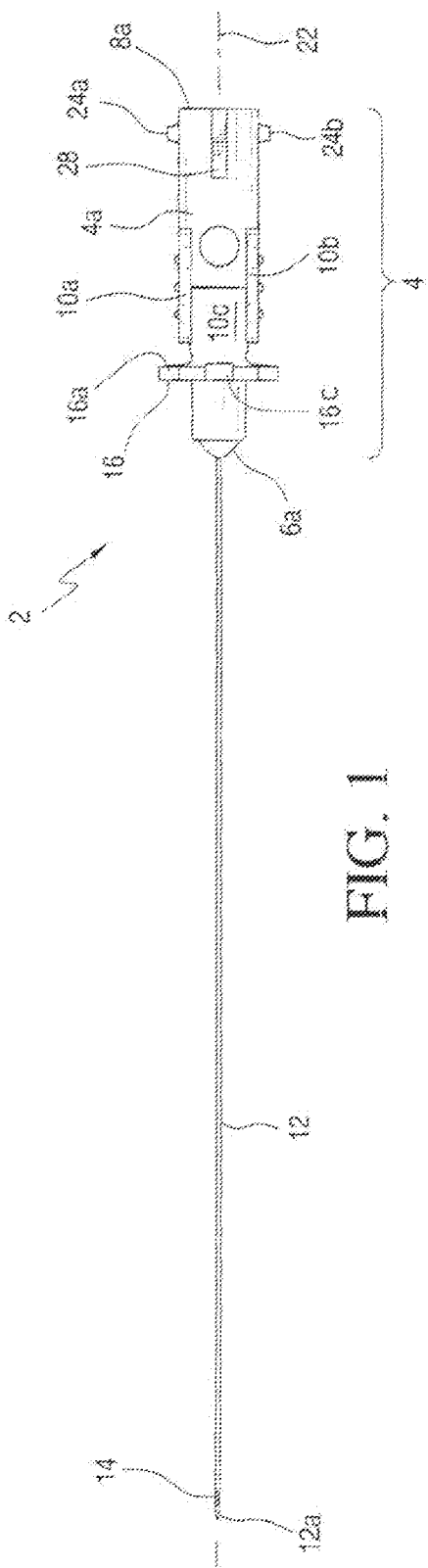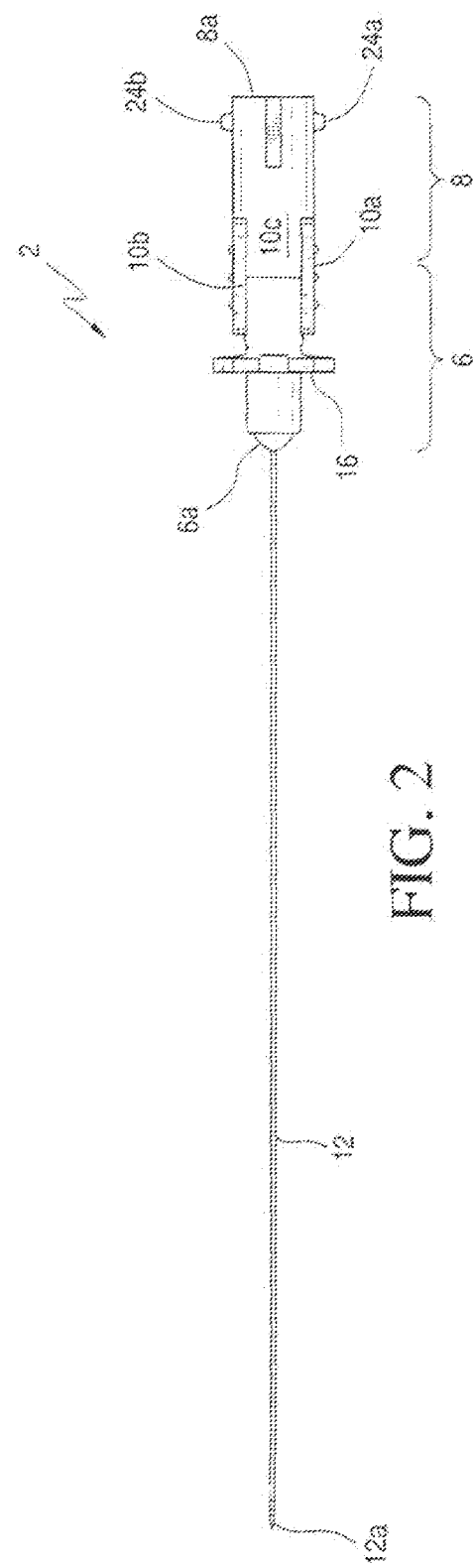

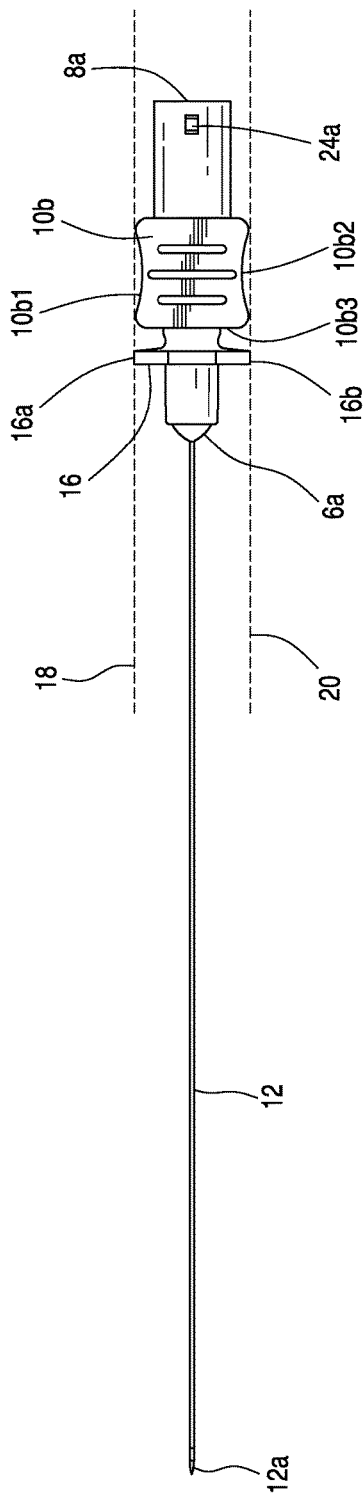
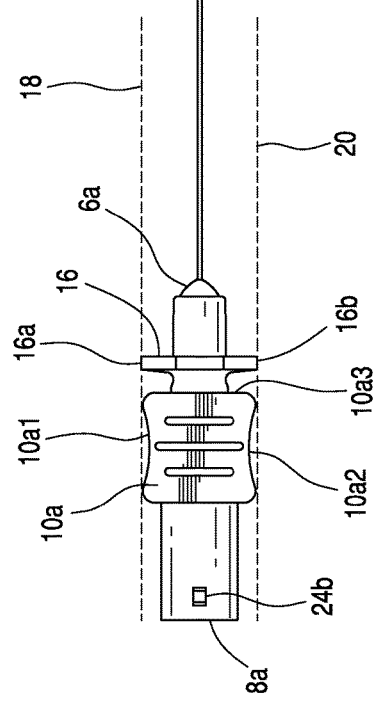
FIG. 3
FIG. 4

NEEDLE ASSEMBLY

FIELD OF THE INVENTION

The present invention relates to needle assemblies, and particularly to a needle assembly that has a specially designed hub that enables a user to firmly grasp and manipulate the needle for insertion to a patient. The connector end of the hub has a non-conventional configuration that prevents the needle hub from connecting to conventional counterpart connectors.

BACKGROUND OF THE INVENTION

Some of the prior art spinal and epidural needles tend to be somewhat difficult to manipulate by a surgeon or anesthesiologist, when inserting the needle into the patient. The prior art does disclose some needle hubs that have means for the user to grasp. Such prior art includes U.S. Pat. Nos. 6,027,480, D378,405, D421,119 and D469,870. However, those needle hubs do not provide means to prevent the user from inadvertently making contact with the needle or guide the insertion of the needle to the patient, or have a connector that prevents mis-connection. The instant invention needle assembly is an improvement of the prior art needle assembles.

SUMMARY OF THE PRESENT INVENTION

The needle assembly of the instant invention has a needle hub that has a main body having a distal portion with a closed distal end to which a needle extends and a proximal portion to which there is an opened proximal end for connection to a fluid store such as a syringe or a fluid line. The body is a substantially cylindrical body with the distal portion sloping downwards from where it merges with the proximal portion towards the closed distal end. Two substantially rectangular plates are formed on opposite sides of the body that bridges the proximal and distal portions. The plates are bonded to the body in a parallel relationship, with the respective upper edges and the respective lower edges being substantially correspondingly coplanar. Accordingly, as the respective upper edges and respective lower edges of the two plates lie along corresponding planes, the needle hub, when placed onto a flat surface with either the respective upper edges or the respective lower edges, would stay put without rolling.

Proximate or adjacent to the two plates there is a partition at the distal portion of the needle hub body formed orthogonally to the longitudinal axis of the needle, and therefore orthogonal to the two plates that are bonded to opposite sides of the main body. The partition has its top edge in substantial coplanar alignment with the upper edges and its bottom edge in substantial coplanar alignment with respective lower edges of the two plates. As a result, upper and lower three point stable supports are provided by the respective edges of the two plates and the partition at their respective upper edges or their respective lower edges. This configuration ensures that when the needle assembly is put on a flat surface, it will not move due to unintentional rolling. In addition to providing additional support, the partition, being positioned at the distal portion of the needle hub, prevents the fingers of the user from inadvertently coming into contact with the needle that extends from the closed distal end.

There is a notch formed at the partition extending from its upper edge inwardly towards the body of the hub to provide a line of sight that extends to the bevel tip of the needle, which may include an orifice that opens on the side of the needle. The notch at the partition provides a line of sight from the needle tip to the space between the upper portion of the two plates which a user can use as a sight guide to insert the needle into the patient.

The opened proximal end of the needle hub forms the connector that connects the needle assembly to the fluid source. The proximal end is configured to have two protuberances that extend on opposite sides at the proximal portion of the body. In addition, the opening at the proximal end is configured such that the connector of the needle hub is matable only to a counterpart connector that has a complementary configuration. Also formed at the proximal end is a keyway that guides the insertion of a stylet into the needle to prevent the coring of the needle during its insertion into the patient.

BRIEF DESCRIPTION OF THE FIGURES

The present invention will become apparent and the invention itself will be best understood with reference to the following description of the present invention taken in conjunction with the accompanying drawings, wherein:

FIG. 1 is a top view of the needle assembly of the instant invention;

FIG. 2 is the bottom view of the inventive needle assembly;

FIG. 3 is one side view of the inventive needle assembly;

FIG. 4 is another side view of the inventive needle assembly;

DETAILED DESCRIPTION OF THE INVENTION

Figure 5:
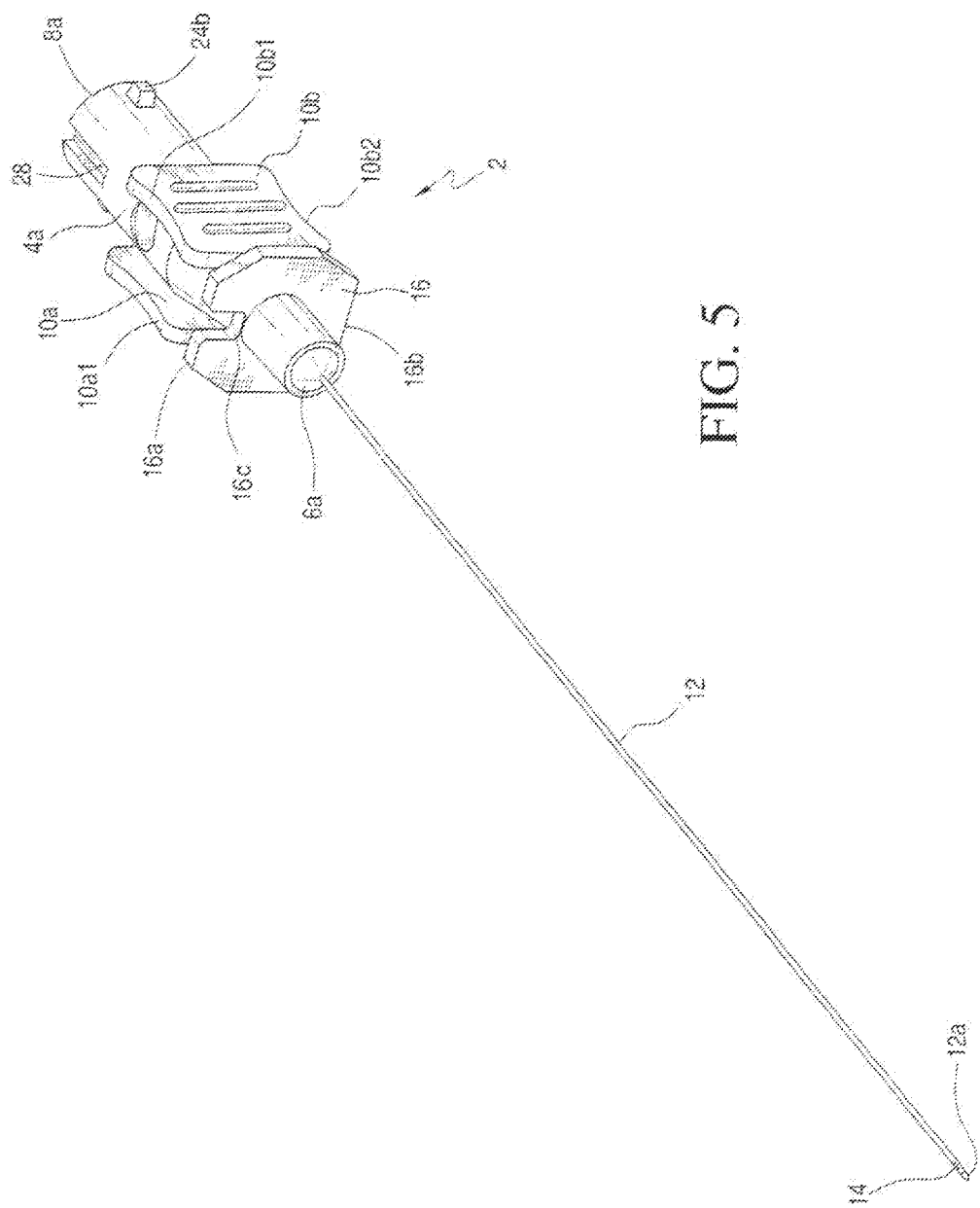
FIG. 5 is a perspective front view of the inventive needle assembly.

With reference to the figures, needle assembly 2 of the instant invention is shown to have a needle hub 4 that includes a distal portion 6 and a proximal portion 8. It should be appreciated that although designated as such in FIG. 2, there is no actual line of demarcation between distal portion 6 and proximal portion 8. Distal portion 6 has a closed distal end 6*a*, whereas proximal portion 8 has an opened proximal end 8*a*. Needle hub 4 has a main body 4*a* that is substantially cylindrical along proximal portion 8 and slopes or inclines downwards in a conical fashion towards distal end 6*a* along distal portion 6.

Two flats or plates 10*a* and 10*b* are bonded to body 4*a* bridging distal portion 6 and proximal portion 8. Plates 10*a* and 10*b* each are substantially rectangular in shape, with their respective upper edges 10*a*1, 10*b*1 and their respective lower edges 10*a*2 and 10*b*2, slightly curved inwardly to form a slight concave configuration. For the instant invention, the respective upper edges 10*a*1 and 10*b*1 of plates 10*a* and 10*b* are deemed to lie substantially co-planarly along an upper plane, designated by dotted line 18 in FIG. 3; and the respective lower edges 10a2 and 10b2 of plates 10a and 10b are deemed to lie substantially co-planarly along a lower plane, designated by dotted line 20 in FIG. 3. Thus, the respective upper edges form one rest support for the needle hub, if the needle hub were to be placed on a flat surface using the respective upper edges 10a1 and 10b1. Likewise, the respective lower edges 10a2 and 10b2 form another rest support whereby the needle can be placed onto a flat surface by using those edges. Once placed onto a flat surface, the respective upper and lower edges each provide support for the needle hub, and prevent the needle hub from rolling. As best shown in FIGS. 1 and 2, plates 10a and 10b are formed in parallel to each other in a relationship that defines a space 10c between the two plates.

At the closed distal end 6a there is extending from needle hub 4 a needle 12. For the embodiment shown in the figures, needle 12 may be a spinal needle that has a closed end 12a and a side opening or orifice 14 proximate to the closed end 12a where through fluid from the needle may traverse. Although a spinal needle with a closed end and a side orifice is shown, it should be appreciated that a spinal needle having an opened end tip is equally applicable for the instant invention.

At distal portion 6 between the respective front edges 10a3 and 10b3 of plates 10a and 10b and distal end 6a there is integrally formed at needle hub 4 a partition plate, or simply a partition 16, orthogonally to the longitudinal axis 22 of the needle assembly. Partition 16 therefore is orthogonal to plates 10a and 10b, and provides a stop for the fingers (defined to include the thumb) of a clinician user, if the user is grasping plates 10a and 10b with his fingers, for example with his thumb and fore finger. As partition 16 prevents the fingers of the user from inadvertently making contact with needle 12, plates 10a and 10b prevent the needle from rolling between the fingers of the clinician user to ensure that the orientation of the tip of the needle may continuously be monitored by the user.

Partition 16 is substantially rectangular and has an upper edge 16a and a lower edge 16b. As best shown in FIG. 3, upper edge 16a of plate 16 lies in a coplanar relationship with edges 10b1 and 10a1 of plates 10b and 10a, respectively, along plane 18. Similarly, the lower edge 16b of partition 16 lies co-planarly with respective lower edges 10a2 and 10b2 of plates 10a and 10b along plane 20. See FIGS. 3 and 4. As a result, top edge 16a of partition 16 and top edges 10a1 and 10b1 of plates 10a and 10b together form a multiple point stable support for the needle hub 4, were the needle hub to be rested on a flat surface by means of those edges. Likewise, bottom edge 16b of partition 16 and respective bottom edges 10a2 and 10b2 of plates 10a and 10b together provide a multiple point stable support to ensure that the needle hub would not move once it has been placed onto a flat surface supported by those lower edges.

Partition 16 has a notch 16c that extends from its top edge 16a inwardly towards the longitudinal axis 22. Notch 16c is formed such that it provides a line of sight from needle tip 12a to space 10c defined between plates 10a and 10b at the top portion of the needle hub. Notch 16c may act as a sight guide for the user to ensure that the bevel end of the needle, and/or also the side orifice 14, be correctly inserted into the patient. By grasping plates 10a and 10b with his thumb and fore finger and biasing the front portions of those digits against the side of partition 16 that faces plates 10a and 10b, the user can readily manipulate the needle since the rolling of the needle between the fingers of the user is prevented as discussed above. And by using partition 16 as a push plate, with the aid of notch 16c, the orientation of the tip of the needle is continuously monitored as the user guidedly inserts the needle into the patient, so as to ensure the correct placement of the tip of the needle in the patient.

Figure 6:
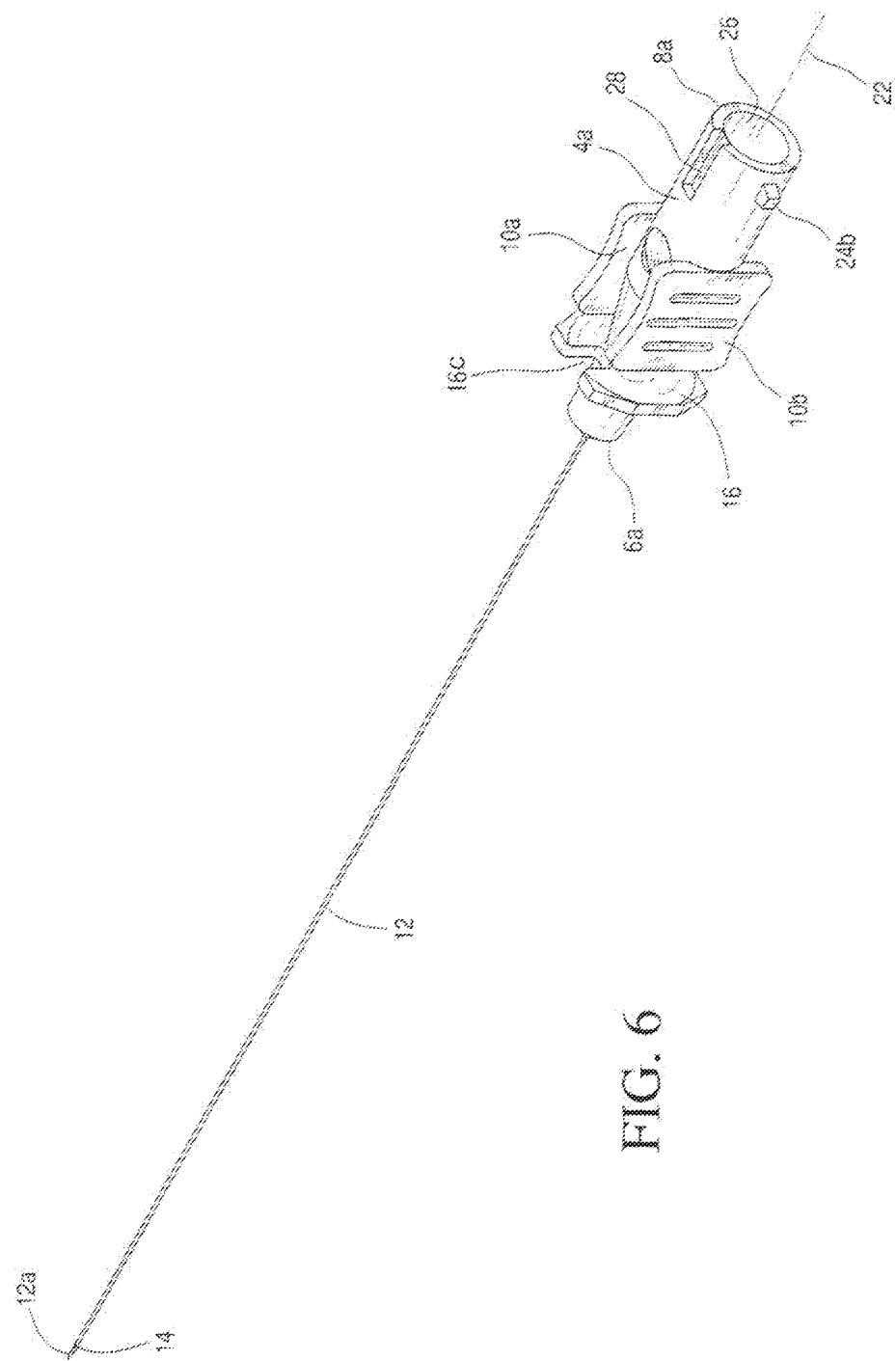
FIG. 6 is a perspective rear view of the inventive needle assembly.

The connector of needle hub 4 is provided at the end of proximal portion 8 close to the opened proximal end 8a. As shown, two protuberances 24a and 24b are provided at opposite sides of the connector at proximal portion 8. The protuberances are configured such that they are engagable only with a counterpart connector that has complementary channels or grooves for accepting them. Also, the opening 26 (FIG. 6) at proximal end 8a has a dimension that allows the connector to only mate with a counterpart non-conventional connector that has a complementary dimensioned opening, so that needle hub 4 will not connect to a counterpart connector that has a conventional luer connector defined by International Standard Organization (ISO) standards. The dimension(s) of an exemplar non-conventional connecter that may be used for the connector portion of the needle assembly of the instant invention may be gleaned from application 61/457,879 filed on Jun. 27, 2011. The disclosure of the '879 application is incorporated by reference to the disclosure of the instant application.

Figures 7A, 7B:
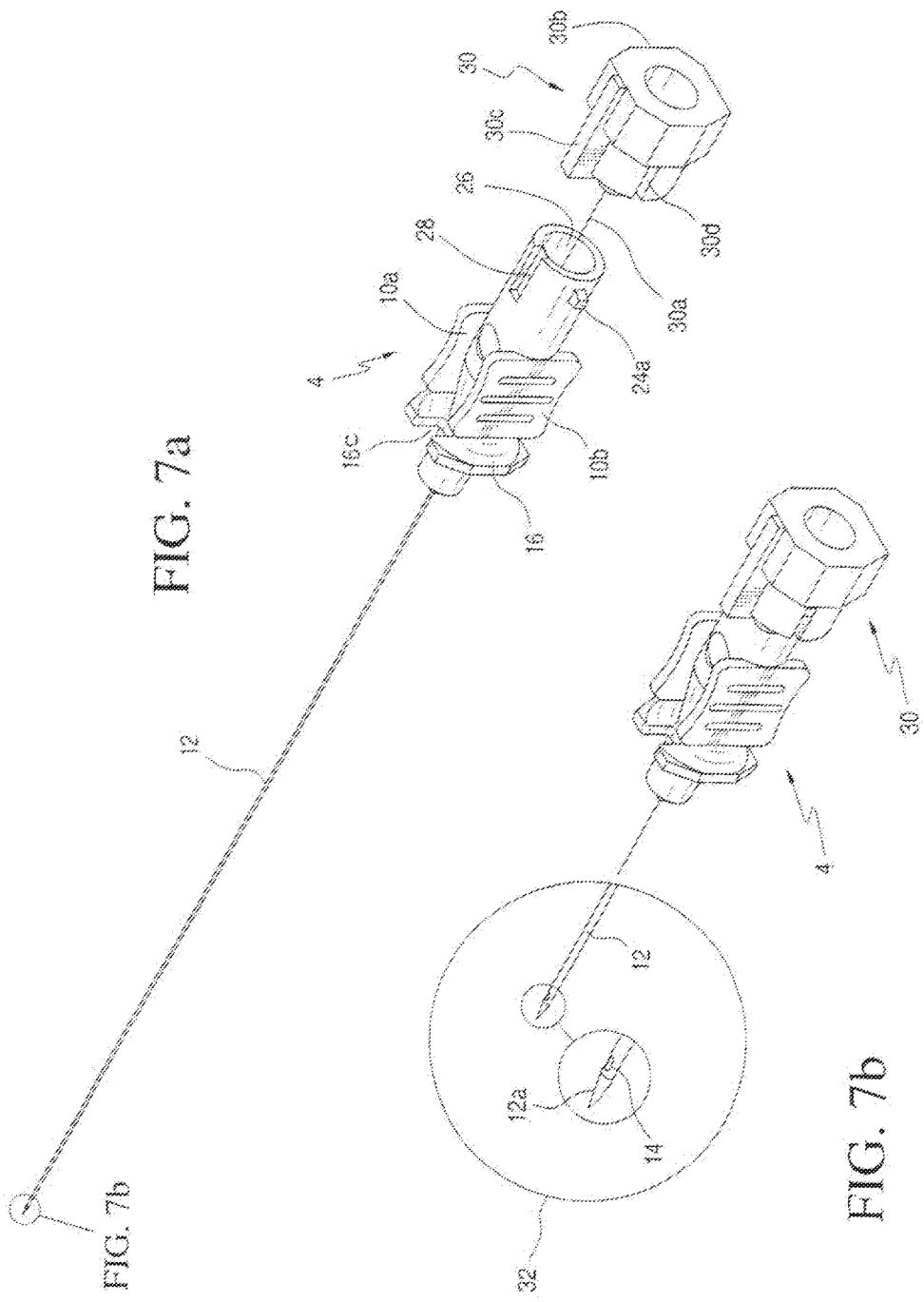
FIG. 7*a* is a perspective view of the needle assembly of the instant invention having the needle of a stylet partially inserted thereinto.
FIG. 7*b* is another perspective view of the needle assembly of the instant invention having inserted therein the needle of the stylet.

A keyway 28 that extends from proximal end 8a inwardly to body 4a along the longitudinal axis 22 provides a guide, at proximal portion 8, for accepting a stylet 30 (FIGS. 7a and 7b) that includes a stylet needle 30a and its hub 30b. As shown, stylet hub 30b has a finger 30c that slidably fits into keyway 28, when stylet hub 30b is fitted to the connector portion of needle hub 4. There are also slots 30d, only one being shown, that allows stylet hub 30b to fit onto proximal portion 8 without interference from protuberances 24a and 24b. With stylet 30 fully inserted into hub 4, per shown in FIG. 7b, side orifice 14 of needle 12, per shown in the exploded view 32 of FIG. 7b, is blocked by stylet needle 30a, so that there would not be any coring by needle 12, when needle 12 is inserted into the patient. Once the needle is properly placed within the patient, stylet 30 is removed, so that medicament may be conveyed to the patient by means of side orifice 14 of needle 12. In the case of an open ended spinal needle, the stylet blocks the opened end of the needle while it is inserted in the needle. It should be appreciate that even though a spinal needle is shown by the figures, an epidural needle (which has an opened end tip) may also be fitted with the inventive needle hub disclosed herein.

Figure 8:
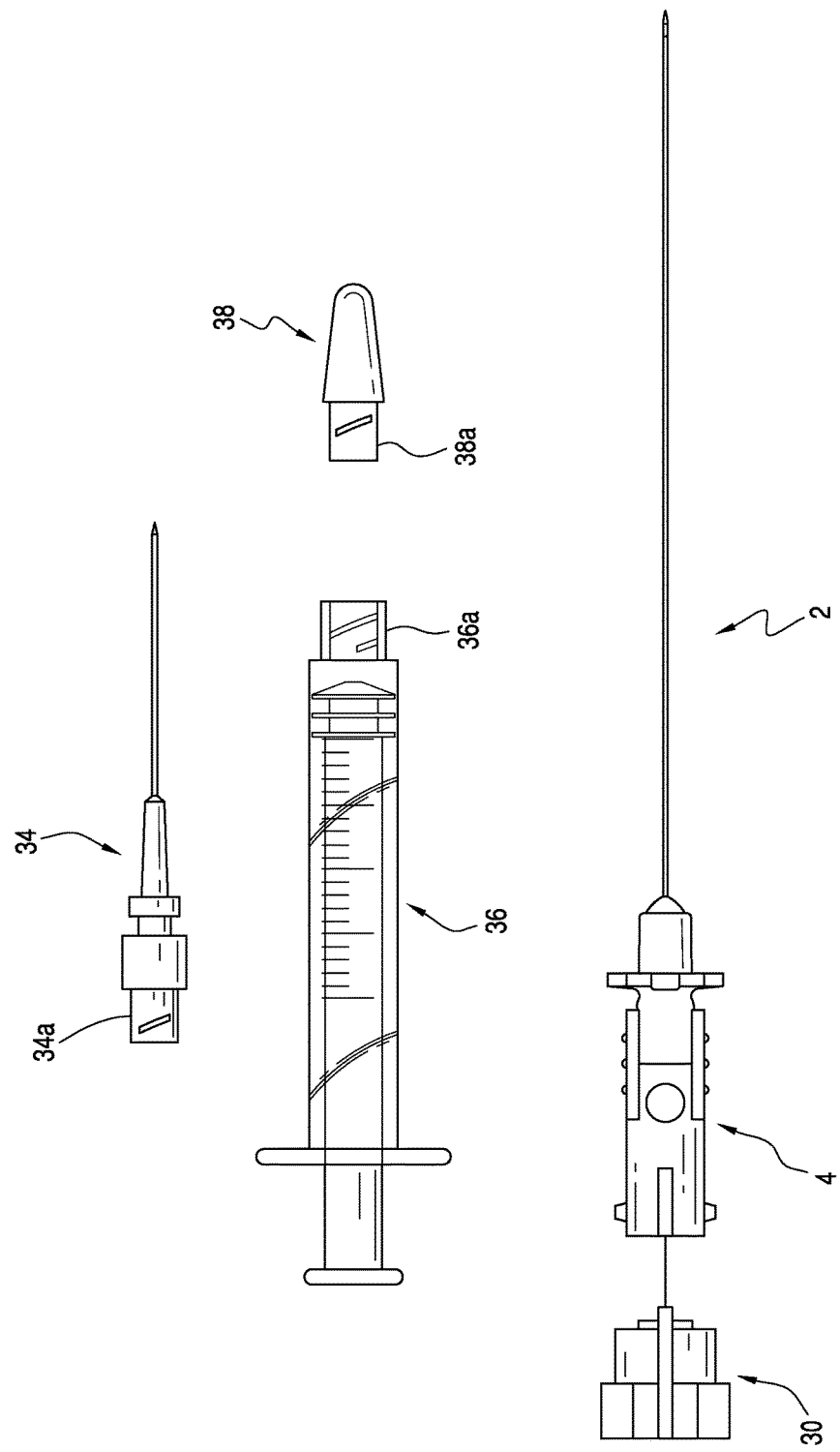
FIG. 8 is an illustration of the needle assembly of the instant invention, and other components that may be used in conjunction therewith.

FIG. 8 shows the various components that may be used with the needle assembly 2 of the instant invention. As shown, there is a syringe 36 provided with a receptacle end 36a having a configuration complementary to the connector portion of needle hub 4. A cap 38 that has a connector portion 38a having a configuration similar to the connecter portion of needle hub 4 is provided to cap the receptacle end 36a of syringe 36, prior to its use, so as to prevent possible contamination thereof. Syringe 36 may be used with a filter needle 34 that has a connector portion 34a dimensionally configured to be connectable to receptacle end 36a of syringe 36.

In use, cap 38 is removed from syringe 36. Needle 34 is then connected to syringe 36 so that medicament may be withdrawn from a vial (not shown) via needle 34 into syringe 36. Thereafter, needle 34 is discarded. Prior to or after the medicament has been withdrawn from the vial into syringe 36, the surgeon or anesthesiologist would insert the needle 12 of needle assembly 2 into the patient, for example spinally or epidurally. Once the needle 12 is correctly positioned in the patient, and after syringe 36 is filled with the appropriate medicament, needle hub 4 and syringe 36 are matingly coupled together so that the medicament stored in the syringe may be conveyed into the patient, in a manner well known in the art for example by pushing the plunger of the syringe. Although FIG. 8 illustrates one exemplar embodiment procedure for utilizing the needle assembly, it should be appreciated that the needle assembly of the instant invention may be an epidural needle having a connector for connection with a syringe for injection, or an epidural needle utilized to place an epidural catheter into the patient, with the epidural catheter connected to a fluid store such as a fluid line or a fluid cassette after the removal of the epidural needle as is well known in the art. The medicament may then be dispensed through the catheter to the patient by a syringe or an infusion pump.

The invention claimed is:

1. Needle assembly, comprising:
a needle hub having a main body along a longitudinal axis having a distal portion and a proximal portion, a needle extending from the distal portion; two plates secured to opposite sides of the distal portion along the longitudinal axis in parallel to each other, the respective top edges and the respective bottom edges of the two plates along the longitudinal axis of the needle hub being in substantial corresponding coplanar alignment so that the respective top edges and the respective bottom edges of the two plates provide corresponding top and bottom supports for the needle hub on a flat surface, the needle hub further having a partition positioned orthogonal to the longitudinal axis of the needle hub proximate to the two plates, the top edge of the partition being in substantial coplanar relationship with the respective top edges of the two plates and the bottom edge of the partition being in coplanar relationship with the respective bottom edges of the two plates so that the top and bottom edges of the partition provide respective additional top and bottom supports for the needle hub on the flat surface; wherein a user can readily and firmly grasp the needle assembly by grasping the respective outer surfaces of the two plates; and wherein the partition provides a stop for the fingers of the user and prevents the fingers from inadvertently making contact with the needle.

2. Needle assembly of claim 1, wherein the proximal portion of the needle hub comprises a connector having an opening, the connector having a non-conventional configuration that enables it to be coupled only to a counterpart connector having a non-conventional complementary configuration but not to a counterpart connector of a conventional configuration.

3. Needle assembly of claim 2, wherein the connector comprises two protuberances formed at opposite sides of the proximal portion proximate to the needle hub, the opening of the connector having a dimension that prevents the connector from mating with a conventional counterpart connector.

4. Needle assembly of claim 2, wherein the connector comprises a keyway to guide the insertion of a stylet into the needle.

5. Needle assembly of claim 1, wherein the partition has a notch that extends inwardly from its top edge, the notch providing a line of sight that extends between the two plates to the tip of the needle, the notch providing a sight guide to the user for correctly inserting the needle into a patient, and the partition provides a stop for the fingers of the user to push the needle into the patient.

6. Needle assembly of claim 1, wherein the needle is a spinal needle.

7. Needle assembly of claim 1, wherein the needle is an epidural needle.

8. Needle assembly, comprising:
a needle;
a hub having a longitudinal axis including an opened proximal end and a closed distal end, the needle extending from the distal end, the hub having
two plates secured to opposite sides of the hub along the longitudinal axis in parallel to each other, the respective top edges and the respective bottom edges of the two plates being in correspondingly substantial co-planar alignment so that the respective top edges and the respective bottom edges of the two plates provide corresponding top and bottom supports along the longitudinal axis for the needle hub on a flat surface,
a partition positioned orthogonal to the longitudinal axis of the hub proximate to the two plates, the top edge of the partition being in substantial coplanar relationship with the respective top edges and the bottom edge of the partition being in substantial coplanar relationship with the respective bottom edges of the two plates;
connector means at the opened proximal end having a non-conventional configuration that enables it to be coupled only to a counterpart connector having a non-conventional complementary configuration but not to a counterpart connector having a conventional configuration.

9. Needle assembly of claim 8, wherein the top and bottom edges of the partition provide respective additional top and bottom supports for the needle hub on the flat surface; and
wherein a user can readily and firmly grasp the needle assembly by grasping the respective outer surfaces of the two plates to insert the needle into a patient.

10. Needle assembly of claim 8, wherein the connector means comprises two protuberances formed at opposite sides of the hub proximate to the opened proximal end, the opened proximal end having a dimension that prevents the connector from mating with a conventional counterpart connector.

11. Needle assembly of claim 8, wherein the partition has a notch that extends inwardly from its top edge, the notch providing a line of sight that extends from a space defined between the two plates to the tip of the needle, the notch providing a sight guide to the user for correctly inserting the needle into a patient, and the partition provides a stop for the fingers of the user to push the needle into the patient and to prevent the fingers of the patient from inadvertently making contact with the needle.

12. Needle assembly of claim 8, wherein the needle is a spinal needle.

13. Needle assembly of claim 8, further comprising a keyway at the opened proximal end to guide the insertion of a stylet into the needle.

14. Needle assembly of claim 8, wherein the needle is an epidural needle.

* * * * *